United States Patent
Altmann

(10) Patent No.: US 6,786,603 B2
(45) Date of Patent: Sep. 7, 2004

(54) WAVEFRONT-GENERATED CUSTOM OPHTHALMIC SURFACES

(75) Inventor: Griffith E. Altmann, Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 109 days.

(21) Appl. No.: 10/254,813

(22) Filed: Sep. 25, 2002

(65) Prior Publication Data

US 2004/0057014 A1 Mar. 25, 2004

(51) Int. Cl.$^7$ ............................................. A61B 3/00
(52) U.S. Cl. ....................................................... 351/246
(58) Field of Search ............................... 351/246, 247, 351/239, 241, 242, 243, 213, 211, 212, 216, 221, 219

(56) References Cited

U.S. PATENT DOCUMENTS 6,338,559 B1 * 1/2002 Williams et al. ............ 351/212
6,511,180 B2 * 1/2003 Guirao et al. ............... 351/211

* cited by examiner

Primary Examiner—George Manuel
(74) Attorney, Agent, or Firm—Craig E. Larson; Denis A. Polyn

(57) ABSTRACT

An embodiment of the invention is directed to a method for determining an anterior or posterior surface parameter of an ophthalmic correcting surface (e.g., custom contact lens "CCL," customized IOL, custom inlay, customized corneal surface) from a wavefront aberration measurement of an eye. A preferred embodiment relates to determining an anterior surface parameter of a dry, CCL designed to operate at 555 nm. An algorithm sets forth the method comprising misalignment correction, chromatic aberration correction, and power shift correction due to differences between aberration measurement wavelength and peak vision wavelength, and differences between aberration measurement location and aberration correction location. A device readable medium is the preferable vehicle for the algorithm.

30 Claims, 4 Drawing Sheets

WAVEFRONT-GENERATED CUSTOM OPHTHALMIC SURFACES

BACKGROUND OF THE INVENTION

1. Field of the Invention

The invention is generally directed to the field of ophthalmic vision correction, and more specifically to wavefront-generated custom ophthalmic surfaces.

2. Description of Related Art

An ocular aberrometer, like the Zywave® wavefront analyzer (Bausch & Lomb Incorporated, Rochester, N.Y.) measures the wavefront aberration exiting a patient's eye at the eye's entrance pupil plane. This is accomplished by injecting a narrow beam of infra-red laser energy into the patient's eye along the patient's visual axis. The wavelength of the Zywave measurement beam is 780 nm. The laser energy diffusely reflects off the patient's fovea and passes back through the eye completely filling the patient's physical pupil. The optical components of the aberrometer relay the image of the physical pupil, which is by definition the entrance pupil, onto a Hartmann-Shack wavefront sensor (HSWFS). The HSWFS samples the wavefront at known intervals and a computer calculates a complete mathematical description of the patient's exiting wavefront aberration. In the case of the Zywave, the mathematical description of the wavefront aberration is in the form of Zernike polynomials per Born & Wolf's notation (Born & Wolf, *Principles of Optics*, 6$^{th}$ Edition, Cambridge University Press (1980 )). This wavefront aberration may be used to design a custom-correction solution for the patient, which may be accomplished through a contact lens, a spectacle, an IOL, an inlay, or laser refractive surgery.

SUMMARY OF THE INVENTION

An embodiment of the invention is directed to a method for determining an anterior or posterior surface parameter of an ophthalmic correcting surface (e.g., custom contact lens "CCL"; customized IOL) from a wavefront aberration measurement of an eye. A preferred aspect of this embodiment relates to determining an anterior surface parameter of a dry, CCL designed to operate at 555 nm. An algorithm sets forth the method comprising misalignment correction, chromatic aberration correction, and power shift correction due to differences between aberration measurement wavelength and peak vision wavelength, and differences between aberration measurement location and aberration correction location. In a preferred aspect directed to determining an anterior surface parameter of a dry, custom-correction contact lens, additional process steps include conversion of aberration polynomial coefficients to wet lens surface deformations, and compensation for dehydration-induced shrinkage.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF A PREFERRED EMBODIMENT

The following detailed description is set forth in terms of data obtained from a Zywave wavefront analyzer (Bausch & Lomb Incorporated, Rochester, N.Y.), however, it is to be appreciated that the invention is not limited in this manner; any accurate mathematical representation of a wavefront aberration would be suitable for practicing the invention. The Zywave incorporates a Hartmann-Shack wavefront sensor (HSWFS) to measure the wavefront aberration exiting a patient's eye at the eye's entrance pupil plane. The retinal illumination source in the Zywave is a diode laser emitting light-having a wavelength of 780 nm. The laser energy diffusely reflects off the patient's fovea and passes back through the eye and into the HSWFS. The HSWFS samples the wavefront at known intervals and a computer calculates a mathematical description of the wavefront aberration as a set of 18 Zernike coefficients ($T_3$ through $T_{20}$) measured in microns. Other data provided by the Zywave include a normalization radius ($R_N$) measured in millimeters, identification of the patient's eye (left or right), equivalent sphere power ($S_E$), and, when applicable, the rotation angle ($\delta$) measured in degrees of a trial lens worn by a patient during measurement. The equivalent sphere power is defined by the equation $$S_E = [R_N^2 + (2*sqrt(3)*T_3)^2] + (2*2*sqrt(3)*T_3),$$

where $T_3$ represents the fourth Zernike term in Born & Wolf notation.

Figure 1:
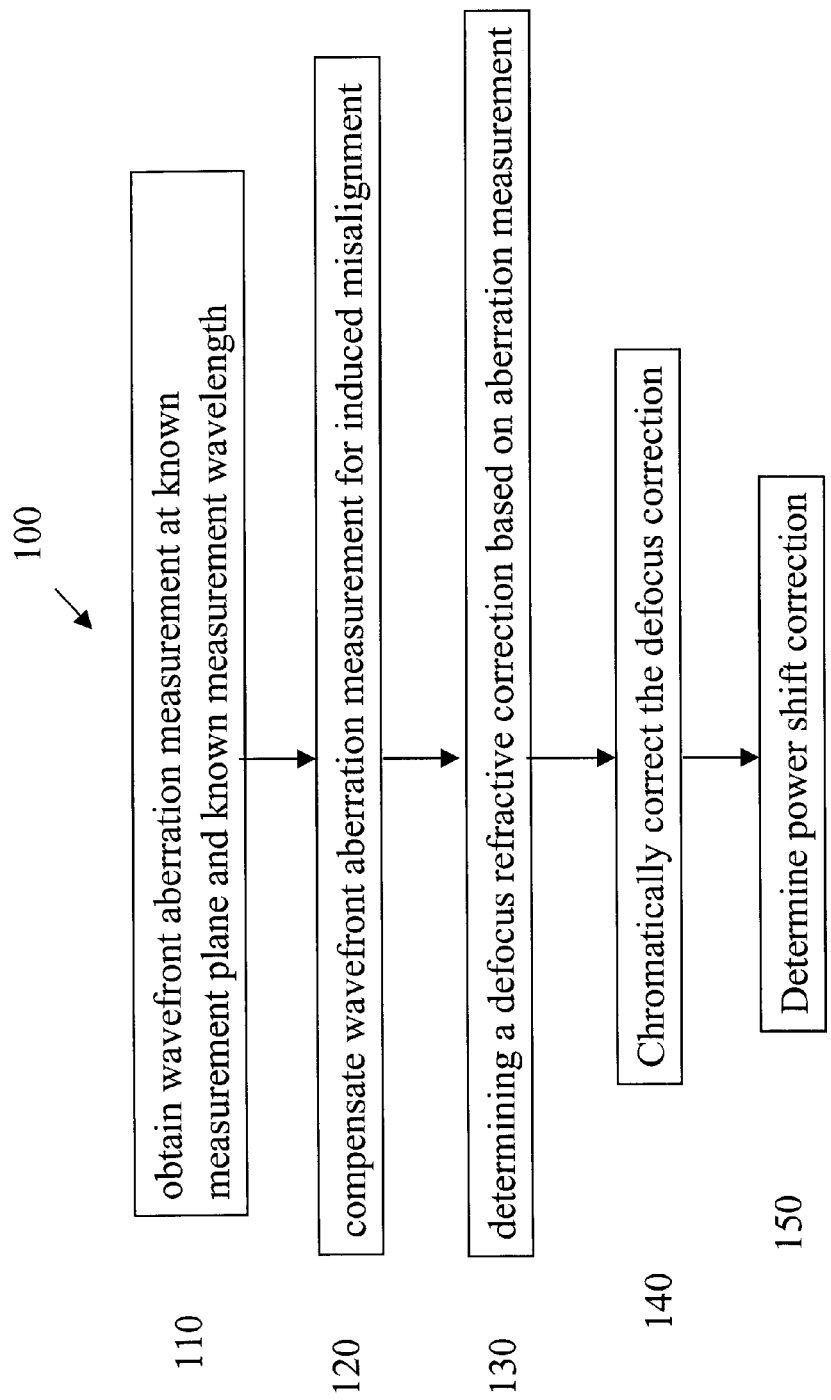
FIG. 1 is a process flow diagram according to an embodiment of the invention.

FIG. 1 shows the process flow steps of an algorithm 100 for determining a surface parameter of an ophthalmic customized correcting surface from a wavefront aberration measurement of an eye. At step 110, a wavefront aberration measurement of the patient's eye is obtained at a known measurement plane location and at a known measurement wavelength. The preferred measurement plane location is the entrance pupil of the patient's eye, and the preferred measurement wavelength is 780 nm so as to minimally affect patient fixation and pupil size. As mentioned above, the Zywave calculates the wavefront aberration in the form of Zernike polynomials per Born & Wolf In a preferred embodiment, the Zernike polynomials are represented by the "Fringe" or University of Arizona notation (see Zemax User's Guide, Version 10.0, pp.124–126). Two differences between the Arizona notation and the Born & Wolf notation are that the polynomial terms are ordered differently, and the B&W notation uses scalar normalization terms in front of the polynomial terms. The first 11 terms of each notation are shown below:

| Term | Arizona Notation | Born & Wolf Notation |
| --- | --- | --- |
| Z1 | 1 | 1 |
| Z2 | $p*\cos(\theta)$ | $2*p*\cos(\theta)$ |
| Z3 | $p*\sin(\theta)$ | $2*p*\sin(\theta)$ |
| Z4 | $2*p^2 - 1$ | $sqrt(3)*(2*p^2 - 1)$ |
| Z5 | $p^2*\cos(2\theta)$ | $sqrt(6)*p^2*\sin(2\theta)$ |
| Z6 | $p^2*\sin(2\theta)$ | $sqrt(6)*p^2*\cos(2\theta)$ |
| Z7 | $(3*p^3 - 2*p)*\cos(\theta)$ | $sqrt(8)*(3*p^3 - 2*p)*\sin(\theta)$ |
| Z8 | $(3*p^3 - 2*p)*\sin(\theta)$ | $sqrt(8)*(3*p^3 - 2*p)*\cos(\theta)$ |
| Z9 | $p^3*\cos(3\theta)$ | $sqrt(8)*p^3*\sin(3\theta)$ |
| Z10 | $p^3*\sin(3\theta)$ | $sqrt(8)*p^3*\cos(3\theta)$ |
| Z11 | $6*p^4 - 6*p^2 + 1$ | $sqrt(5)*(6*p^4 - 6*p^2 + 1)$ |

At step 120, image misalignment is corrected. The wavefront aberration at the patient's entrance pupil is rotated 180 degrees before it reaches the HSWFS. Thus, the Zernike coefficients must be modified in order to account for this rotation. This is done by multiplying all coefficients with odd-theta dependence by −1. Those coefficients with no theta dependence or even-theta dependence are not modified.

At step 130, the equivalent sphere power, $S_E$, is calculated by $$S_E = [R_N^2 + (2*\text{sqrt}(3)*T_3)^2] + (2*2*\text{sqrt}(3)*T_3),$$

where $T_3$ represents the fourth Zernike term in Born & Wolf notation. However, the measurement wavelength 780 nm focuses deeper into the eye than does light at 555 nm, which is the center of the wavelength region for normal human vision. Thus, the Zywave erroneously measures a patient's necessary correction by +0.45 D different from their actual necessary correction. This correction is made at step 140. The correct power adjustment is represented as $B = S_E − 0.45$. Defocus is primarily defined by the fourth Zernike term, $T_3$, therefore, $T_3$ must be modified to account for this known chromatic aberration. If ocular biometry data are collected, then the 0.45 D defocus shift to convert from 780 to 555 nm could be optimized for individual patients on a case-by-case basis. Ocular biometry includes corneal topography or keratometry, axial length of the eye and, optionally, thickness of the crystalline lens. From these measurements, a more precise calculation of longitudinal chromatic aberration can be performed.

At step 150, the algorithm accounts for the power shift due to the measurement being taken at the patient's entrance pupil but the correction being done at the ophthalmic correction surface, such as a modified corneal surface, a custom contact lens surface, a customized IOL surface, a customized inlay surface, or a spectacle surface.

Figure 2:
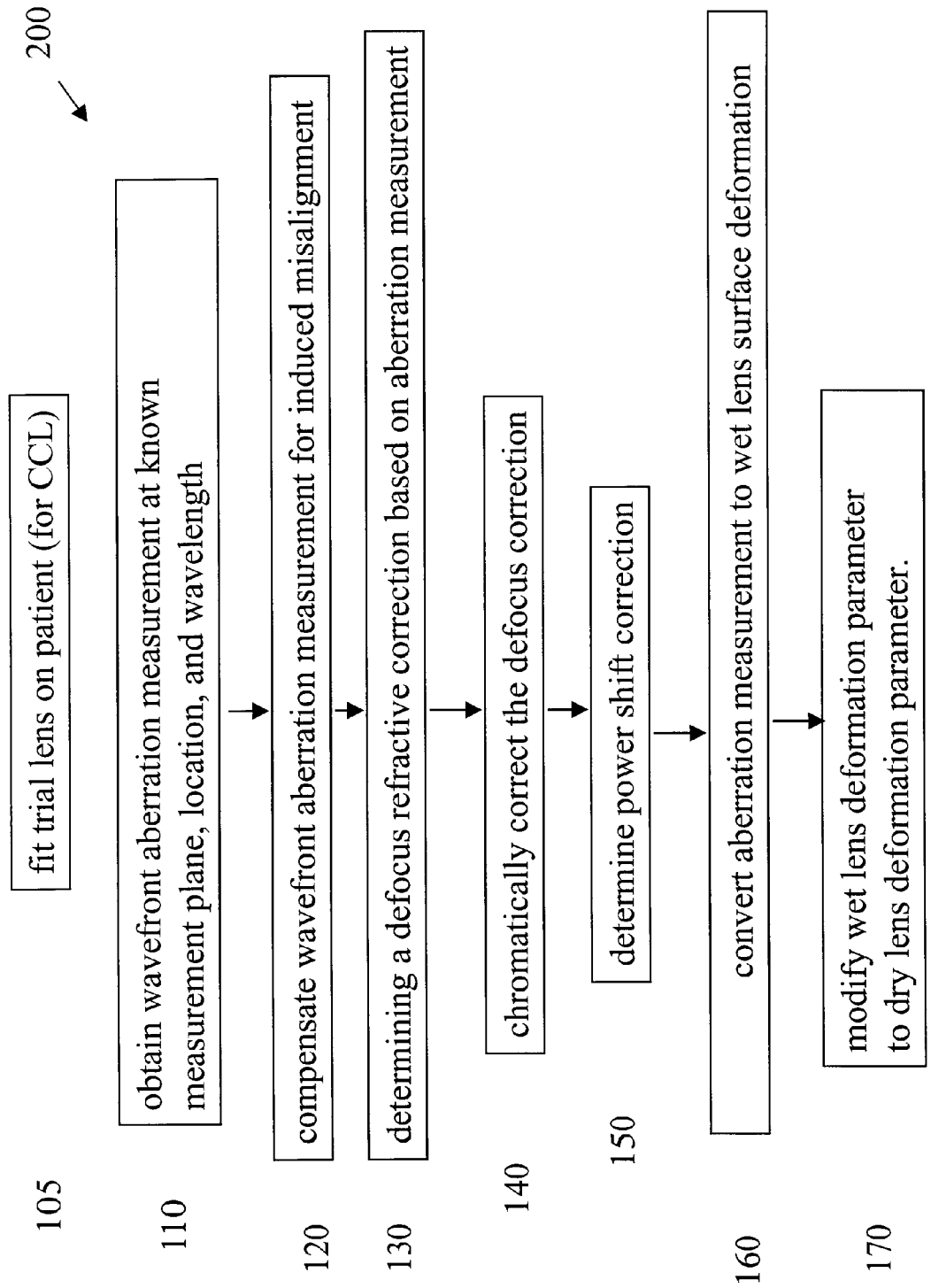
FIG. 2 is a process flow diagram according to a preferred aspect embodiment of the invention.

In a preferred aspect of the embodiment described above, the method is directed to determining an anterior surface parameter of a dry-form CCL designed to operate at 555 nm, from a wavefront aberration measurement of an eye. The method 200 is set forth in FIG. 2. Process steps 110 through 150 remain unchanged but the correction is done at the anterior surface of the contact lens. The 3-D sag profile of the anterior surface of a dry custom-correction contact lens is described by the equation:

$$\text{3-D Sag} = (r^2/R_d)/(1 + \text{sqrt}(1 − r^2/R_d^2)) + \Sigma(Z_i P_i)$$

where r is the radial coordinate, $R_d$ is the dry radius of the anterior surface, $Z_i$ is a set of Zernike coefficients, $P_i$ is a set of Zernike polynomials, and $i \in [4, 27]$. The Zernike coefficients and polynomials are of the Fringe or University of Arizona notation.

The entrance pupil of a typical human eye is located 3.1 mm from the anterior surface of the cornea into the eye. A typical custom contact lens has a center thickness of 0.16 mm. Thus, the correction is located 3.26 mm away from the entrance pupil, and this distance causes a slight power shift between measured power error and the correcting power. This shift is explained by the following equation, where B is the measured power and C is the correcting power located 3.26 mm away from the measurement plane.

$$C = B − 0.00326 * B^2.$$

At step 160, the Zernike coefficients are converted from wavefront deformations to wet lens surface deformations. All coefficients are divided by (n−1), where n is the index of refraction of the wet contact lens material at 555 nm.

At step 170, the algorithm modifies the surface parameter to mathematically reverse hydration-induced expansion in going from wet lens parameters to dry lens parameters. All coefficients are divided by an empirically obtained sag expansion (sag_exp) factor for the lens material. The normalization radius is divided by the empirically obtained diameter expansion (dia_exp) factor. Both of these factors typically range between about 4% to 35% depending upon the lens material.

Figure 3:
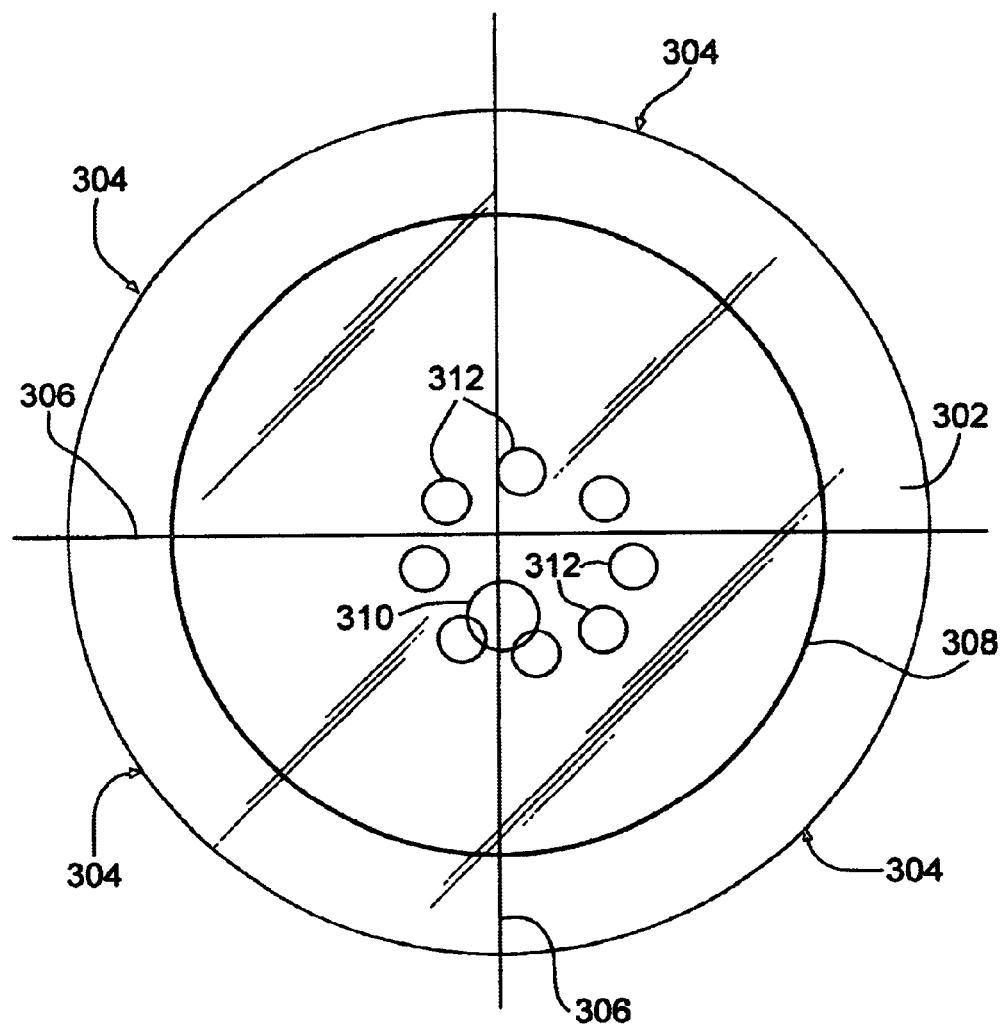
FIG. 3 is a copy of a wavefront sensor eye measurement image illustrating the centration of the wavefront measurement on the optical zone (OZ) of a lens.
Figure 4:
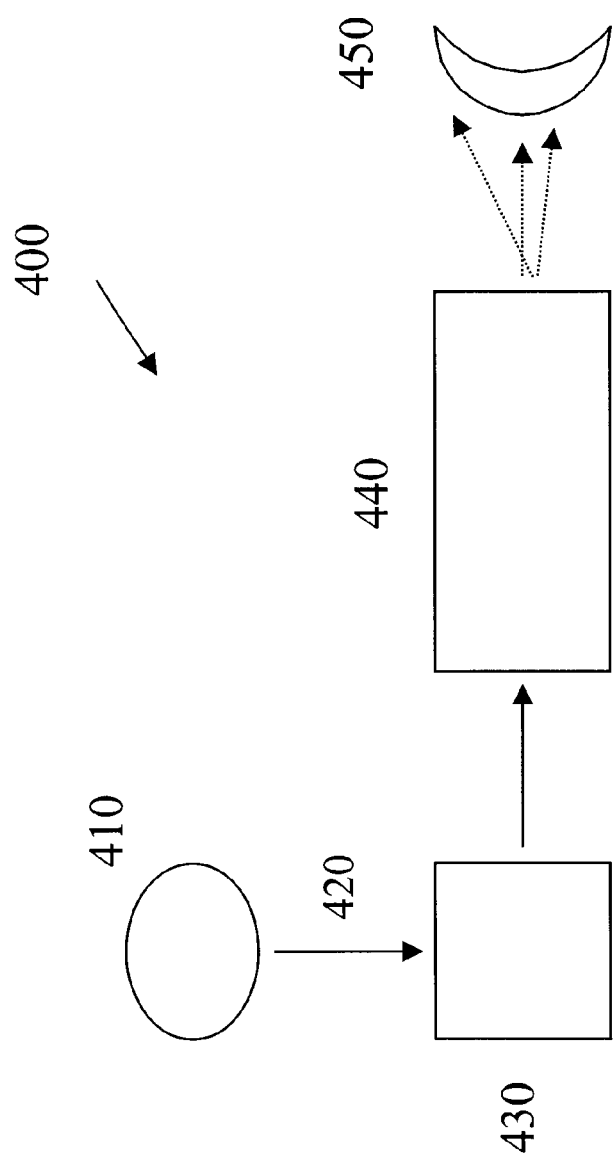
FIG. 4 is a line drawing of a hardware configuration embodiment of the invention.

A Summary of Modified Zernike Coefficients and Normalization Radius is presented as follows:

$N_R' = N_R/\text{dia\_exp}$
$Z4 = T3' * \text{sqrt}(3)/(n−1)/1000/\text{sag\_exp}$
$Z5 = T5 * \text{sqrt}(6)/(n−1)/1000/\text{sag\_exp}$
$Z6 = T4 * \text{sqrt}(6)/(n−1)/1000/\text{sag\_exp}$
$Z7 = T7 * (−1) * \text{sqrt}(8)/(n−1)/1000/\text{sag\_exp}$
$Z8 = T6 * (−1) * \text{sqrt}(8)/(n−1)/1000/\text{sag\_exp}$
$Z9 = T10 * \text{sqrt}(5)/(n−1)/1000/\text{sag\_exp}$
$Z10 = T9 * (−1) * \text{sqrt}(8)/(n−1)/1000/\text{sag\_exp}$
$Z11 = T8 * (−1)\text{sqrt}(8)/(n−1)/1000/\text{sag\_exp}$
$Z12 = T11 * \text{sqrt}(10)/(n−1)/1000/\text{sag\_exp}$
$Z13 = T12 * \text{sqrt}(10)/(n−1)/1000/\text{sag\_exp}$
$Z14 = T15 * (−1) * \text{sqrt}(12)/(n−1)/1000/\text{sag\_exp}$
$Z15 = T16 * (−1) * \text{sqrt}(12)/(n−1)/1000/\text{sag\_exp}$
$Z16 = (\text{not currently used}).$
$Z17 = T13 * \text{sqrt}(10)/(n−1)/1000/\text{sag\_exp}$
$Z18 = T14 * \text{sqrt}(10)/(n−1)/1000/\text{sag\_exp}$
$Z19 = T17 * (−1) * \text{sqrt}(12)/(n−1)/1000/\text{sag\_exp}$
$Z20 = T18 * (−1) * \text{sqrt}(12)/(n−1)/1000/\text{sag\_exp}$
$Z21 = T23 * \text{sqrt}(14)/(n−1)/1000/\text{sag\_exp}$
$Z22 = T22 * \text{sqrt}(14)/(n−1)/1000/\text{sag\_exp}$
$Z23 = (\text{not currently used})$
$Z24 = (\text{not currently used})$
$Z25 = (\text{not currently used})$
$Z26 = T19 * (−1) * \text{sqrt}(12)/(n−1)/1000/\text{sag\_exp}$
$Z27 = T20 * (−1) * \text{sqrt}(12)/(n−1)/1000/\text{sag\_exp}$ In an exemplary aspect of the preferred embodiment, the patient is fitted with a prism- or peri-ballasted spherical trial lens of known geometry. The power of the trial lens may be plano or may match the patient's spherical-equivalent refraction. The latter is most preferred. The trial lens preferably will be made of the same material as the CCL. The base curve of the trial lens, possibly chosen to include a plurality of base curves, will be matched to the patient's needs, similar to the CCL. The wavefront aberration is measured while the patient wears the trial lens. The measurement is centered on the center of the OZ of the trial lens, which is where the custom lens modifications will be centered. This step is depicted at 105 in FIG. 2. The measurement thus takes into account effects such as, for example, lens tilt and decentration, lens deformation as it adheres to the cornea, tear film effects, lens rotation, etc. It is often difficult to see the OZ on a lens while the patient is wearing it, and likewise when viewing the lens with the aberrometer camera. Furthermore, in a prism-ballasted lens, the OZ is decentered relative to the geometric center of the lens. Thus, it is preferable to mark the OZ such that it will be visible when viewed through the wavefront sensor. In a preferred aspect, illustrated in FIG. 3, the trial lens 302 is indexed with a lathe mark 304 in the form of a ring having a 7.3 mm dry inner diameter, that is centered on the OZ of the lens. The ring was made with a 1 mm tip radius cutting tool. Other ring dimensions or index markings made by lathe cuts, laser inscription, or other means known in the art may also provide suitable centering marks. Moveable crosshairs 306 in the wavefront sensor device are centered on the wavefront measuring beam, and a variable circular indexing mark 308 is also centered in the crosshairs. The diameter of ring 308 is changed until it coincides with the lathe ring mark 304. The wavefront measurement is thus centered on the OZ of the trial lens. In FIG. 3, small circle 310 shows the measurement beam entry location on the eye, but is not relevant to an understanding of the instant invention. Likewise, bright spots 312 are instrument LED reflections from the cornea and are not relevant to the instant invention. Alternatively, the OZ of the trial lens can be encircled with a ring or dots of indelible, FDA-approved ink placed every 15 or 30 degrees on the lens in the dry state. Thereafter, the amount and direction (CW or CCW) of the lens rotation is measured and accounted for during the manufacturing of the lens. The conversions for the rotation adjusted Zernike fringe coefficients in dry lens units are:

(adjusted normalization radius=normalization radius)

$A4=Z'4$ $A5=Z'5* \cos(2*d)-Z'6* \sin(2*d)$ $A6=Z'5* \sin(2*d)+Z'6* \cos(2*d)$ $A7=Z'7* \cos(d)-Z'8* \sin(d)$ $A8=Z'7* \sin(d)+Z'8* \cos(d)$ $A9=Z'9$ $A10=Z'10* \cos(3*d)-Z'11* \sin(3*d)$ $A11=Z'10* \sin(3*d)+Z'11* \cos(3*d)$ $A12=Z'12* \cos(2*d)-Z'13* \sin(2*d)$ $A13=Z'12* \sin(2*d)+Z'13* \cos(2*d)$ $A14=Z'14* \cos(d)-Z'15* \sin(d)$ $A15=Z'14* \sin(d)+Z'15* \cos(d)$ $A16=Z'16$ $A17=Z'17* \cos(4*d)-Z'18* \sin(4*d)$ $A18=Z'17* \sin(4*d)+Z'18* \cos(4*d)$ $A19=Z'19* \cos(3*d)-Z'20* \sin(3*d)$ $A20=Z'19* \sin(3*d)+Z'20* \cos(3*d)$ $A21=Z'21* \cos(2*d)-Z'22* \sin(2*d)$ $A22=Z'21* \sin(2*d)+Z'22* \cos(2*d)$ $A23=Z'23* \cos(d)-Z'24*\sin(d)$ $A24=Z'23* \sin(d)+Z'24*\cos(d)$ $A25=Z'25$ $A26=Z'26* \cos(5*d)-Z'27* \sin(5*d)$ $A27=Z'26* \sin(5*d)+Z'27* \cos(5*d)$ The hardware configuration of a device embodiment 300 of the invention is shown in the block diagram of FIG. 3. A device readable medium 310 includes an algorithm 320 (i.e., a computable set of steps to achieve a desired result) for determining a surface parameter of an ophthalmic correcting surface from a wavefront measurement of an eye, as described in detail above. The device readable medium can take any well known form such as a disk or diskette, CD, DVD, waveguide, etc. that can carry the algorithm 320. The device 330 is preferably a P.C. that is connected to a surface machining apparatus 340. For a CCL, IOL, or in-vitro inlay (all 350), the apparatus 340 is preferably a numerically controlled, multi-axis lathe such as an Optoform 50/Variform® lathe (Precitech, Keene, N.H., USA), or an excimer laser system. For corneal refractive surgery or an in-vivo inlay (all 350), the apparatus 340 preferably is an excimer laser system.

While various advantageous embodiments have been chosen to illustrate the invention, it will be understood by those skilled in the art that changes and modifications can be made therein without departing from the scope of the invention as defined in the appended claims.

I claim:

1. A method for determining a surface parameter of an ophthalmic correcting surface from a wavefront aberration measurement of an eye, comprising:

a) obtaining a wavefront aberration measurement of a patient's eye at a known measurement plane location using a known measurement wavelength;

b) correcting the wavefront aberration measurement as necessary to compensate for a measurement device-induced misalignment of the measurement;

c) determining a defocus refractive correction based upon the aberration measurement;

d) determining a chromatic aberration correction for the defocus correction; and e) determining a power shift correction to account for a correction surface location different from the measurement plane location.

2. The method of claim 1, comprising determining an anterior surface parameter.

3. The method of claim 1, wherein the step of obtaining a wavefront aberration measurement comprises generating an aberration-describing polynomial having associated coefficients.

4. The method of claim 3, wherein the polynomial is a Zernike polynomial.

5. The method of claim 1, wherein the step of obtaining a wavefront aberration measurement comprises making the measurement at a wavelength of 780 nm.

6. The method of claim 1, wherein the step of obtaining a wavefront aberration measurement comprises making the measurement through a trial lens engaged with the patient's eye.

7. The method of claim 6, wherein the ophthalmic correcting surface is an anterior surface of a dry, custom-correction contact lens, designed to operate at 555 nm, further comprising:

converting the aberration measurement from a wavefront deformation to a wet lens surface deformation; and modifying a wet lens deformation parameter to obtain a corresponding dry lens deformation parameter.

8. The method of claim 1, comprising making the measurement through a center of an optical zone of the trial lens.

9. The method of claim 1, wherein the known measurement plane is an entrance pupil plane of the patient's eye.

10. The method of claim 1, wherein the correcting step comprises correcting for device-induced rotation of the aberration measurement.

11. The method of claim 1, wherein the step of determining a power shift correction comprises a correction surface including one surface of a custom contact lens, a custom IOL, a custom inlay, or a customized corneal surface.

12. The method of claim 1, comprising an anterior surface.

13. The method of claim 1, wherein the step of determining a chromatic aberration correction comprises correcting for a design operation wavelength of 555 nm.

14. The method of claim 1, wherein the step of determining a chromatic aberration correction comprises obtaining and using an ocular biometric measurement to optimize the chromatic aberration correction.

15. The method of claim 14, wherein the ocular biometric measurement includes one of a corneal topography measurement, a kerotometry measurement, an axial length measurement of the eye, and a crystalline lens thickness measurement.

16. A device readable medium including an executable instruction for performing an algorithm for determining a surface parameter of an ophthalmic correcting surface from a wavefront measurement of an eye, wherein the algorithm comprises the process steps (b)–(e) according to claim 1.

17. The device readable medium of claim 16, wherein the algorithm is for determining an anterior surface of a dry, custom-correction contact lens, designed to operate at 555 nm.

18. The device readable medium of claim 17, wherein the algorithm further comprises the process steps of:
converting the aberration measurement from a wavefront deformation to a wet lens surface deformation; and
modifying a wet lens deformation parameter to obtain a corresponding dry lens deformation parameter.

19. The device readable medium of claim 16, wherein the algorithm is for determining an anterior surface of one of a custom-correction contact lens, an IOL, an inlay, and a corneal surface.

20. A method for determining a surface parameter of an anterior surface of a dry, custom-correction contact lens, designed to operate at 555 nm, from a wavefront aberration measurement of an eye, comprising:
fitting a trial lens on a patient's eye;
making a wavefront measurement through a central optical zone region of the trial lens, and at a selected measurement plane location using a known measurement wavelength;
determining an amount and direction of rotation of the trial lens on the patient's eye;
correcting the wavefront aberration measurement as necessary to compensate for a measurement device-induced misalignment of the measurement;
determining a defocus refractive correction based upon the aberration measurement;
determining a chromatic aberration correction for the defocus correction;
determining a power shift correction to account for a correction surface location different from the measurement plane location;
converting the aberration measurement from a wavefront deformation to a wet lens surface deformation; and
modifying a wet lens deformation parameter to obtain a corresponding dry lens deformation parameter.

21. The method of claim 20, comprising fitting a prism- or a peri-ballasted trial lens.

22. The method of claim 20, wherein the step of obtaining a wavefront aberration measurement comprises generating an aberration-describing polynomial having associated coefficients.

23. The method of claim 22, wherein the polynomial is a Zernike polynomial.

24. The method of claim 20, wherein the step of obtaining a wavefront aberration measurement comprises making the measurement at a wavelength of 780 nm.

25. The method of claim 20, wherein the step of obtaining a wavefront aberration measurement comprises making the measurement through a trial lens engaged with the patient's eye.

26. The method of claim 25, comprising making the measurement through a central optical zone of the trial lens.

27. The method of claim 20, wherein the known measurement plane is an entrance pupil plane of the patient's eye.

28. The method of claim 20, wherein the correcting step comprises correcting for device-induced rotation of the aberration measurement.

29. The method of claim 20, wherein the step of determining a chromatic aberration correction comprises obtaining and using an ocular biometric measurement to optimize the chromatic aberration correction.

30. The method of claim 20, wherein the ocular biometric measurement includes one of a corneal topography measurement, a kerotometry measurement, an axial length measurement of the eye, and a crystalline lens thickness measurement.

* * * * *